United States Patent
Raeckers et al.

(10) Patent No.: US 9,885,651 B2
(45) Date of Patent: Feb. 6, 2018

(54) METHOD FOR TESTING THE FRACTURE TOUGHNESS OF AN ADHESIVE JOINT TO BE FORMED

(71) Applicant: Airbus Operations GmbH, Hamburg (DE)

(72) Inventors: Bernd Raeckers, Hamburg (DE); Lutz Wiese, Hamburg (DE)

(73) Assignee: AIRBUS OPERATIONS GMBH, Hamburg (DE)

( * ) Notice: Subject to any disclaimer, the term of this patent is extended or adjusted under 35 U.S.C. 154(b) by 102 days.

(21) Appl. No.: 14/813,295

(22) Filed: Jul. 30, 2015

(65) Prior Publication Data
US 2016/0033388 A1   Feb. 4, 2016

(30) Foreign Application Priority Data
Aug. 4, 2014  (DE) .......................... 10 2014 111 060

(51) Int. Cl.
*G01N 3/08* (2006.01)
*G01N 19/04* (2006.01)

(52) U.S. Cl.
CPC ............... *G01N 19/04* (2013.01); *G01N 3/08* (2013.01)

(58) Field of Classification Search
None
See application file for complete search history.

(56) References Cited

U.S. PATENT DOCUMENTS

| | | | |
|---|---|---|---|
| 6,117,695 A | 9/2000 | Murphy et al. | |
| 7,497,115 B2 * | 3/2009 | Menendez Martin | G01N 19/04 73/150 A |
| 2005/0006526 A1 * | 1/2005 | McBroom | B29C 73/24 244/119 |
| 2006/0159513 A1 * | 7/2006 | Breuer | F16B 11/006 403/27 |
| 2008/0011075 A1 | 1/2008 | Menendez et al. | |
| 2011/0283767 A1 | 11/2011 | Questo et al. | |

FOREIGN PATENT DOCUMENTS

| | | | |
|---|---|---|---|
| CA | 2530901 A1 * | 6/2006 | ............ F16B 11/006 |
| DE | 9017803 | 4/1992 | |
| DE | 102004063098 | 7/2006 | |
| DE | 60212996 | 11/2006 | |
| EP | 2040057 | 3/2009 | |
| JP | 2007309470 A * | 11/2007 | |
| WO | 03055747 | 7/2003 | |

OTHER PUBLICATIONS

European Search Report, Dec. 16, 2015.
German Search Report, Aug. 4, 2014.

* cited by examiner

*Primary Examiner* — Andre Allen
(74) *Attorney, Agent, or Firm* — Greer, Burns & Crain, Ltd.

(57) ABSTRACT

A method for testing the fracture toughness of an adhesive joint to be formed between two components made of fiber-reinforced plastic, by forming a test joint between two sample elements and applying a tensile load onto this test joint until a pre-defined value is reached. One of these sample elements is formed by one of the components of the joint to be formed, and the tensile load acts on the other sample element.

9 Claims, 1 Drawing Sheet

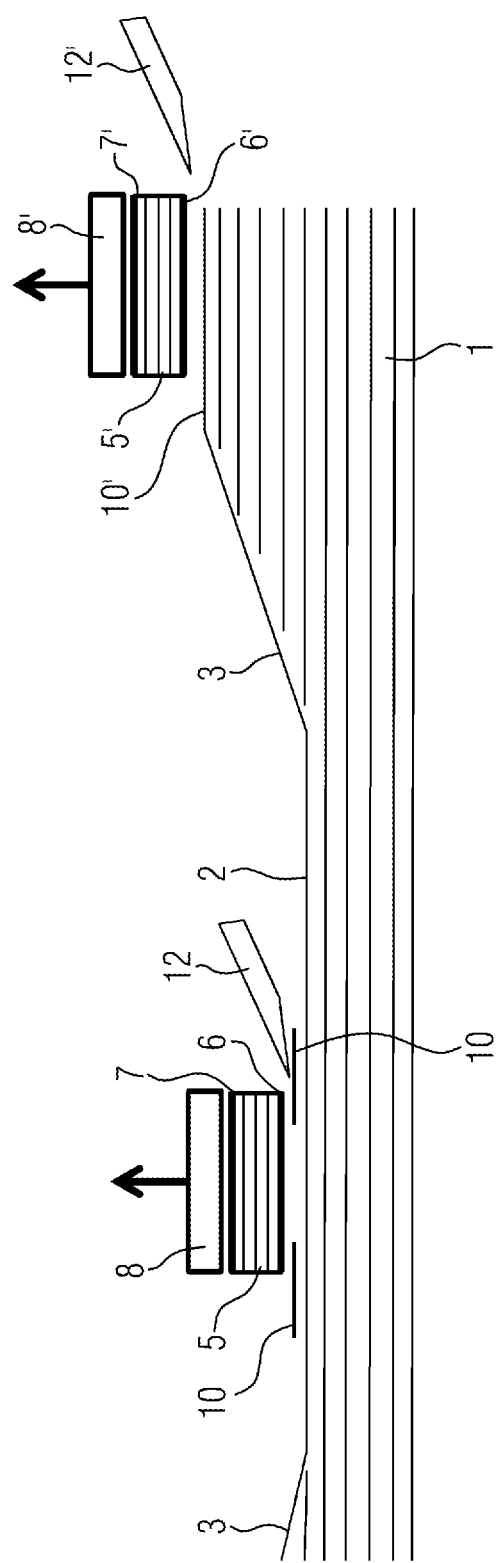

METHOD FOR TESTING THE FRACTURE TOUGHNESS OF AN ADHESIVE JOINT TO BE FORMED

CROSS-REFERENCES TO RELATED APPLICATIONS

This application claims the benefit of the German patent application No. 10 2014 111 060.9 filed on Aug. 4, 2014, the entire disclosures of which are incorporated herein by way of reference.

BACKGROUND OF THE INVENTION

The invention relates to a method for testing the fracture toughness of an adhesive joint to be formed between two components made of fiber-reinforced plastic (FRP) by forming a test joint between two sample elements and applying a tensile load onto this test joint until a pre-defined value is reached.

A number of variations of such methods are known. In one known tensile bond test, for example, two sample elements made of the same material as the components to be joined are adhered to one another, and the outer surfaces of the sample elements are joined by means of adhesive by one testing stamp in each case. By means of these testing stamps, a tensile force is applied to the samples, which is increased until either the joint breaks or a pre-defined limit value, seen as required for the adhesive force of the adhesive joint, is reached. Based on the test result, the strength of an adhesive joint formed between the components to be joined is determined.

In another known method, two sample elements are joined to one another by means of adhesive, and then, by introduction of a wedge element between the sample elements, the level of force that has to be applied to the wedge element in order to separate the samples from one another is determined.

SUMMARY OF THE INVENTION

An objective of the invention is to create a method for testing the fracture toughness of an adhesive joint to be formed, which method is easily carried out and takes greater consideration of the influence on the adhesive joint of the characteristics of the components to be joined.

In order to achieve this objective, a method of the aforementioned kind is designed according to the invention in such a way that one of the sample elements is said one component of the joint to be formed, and the tensile load acts on the other sample element. The other sample element can be circular and can preferably have a diameter of 8 mm to 60 mm, particularly preferably of 10 mm to 50 mm.

In the method according to the invention, the testing of the fracture toughness of the adhesive joint to be formed is thus carried out directly on one of the components which is to be joined to another component, which means that the surface characteristics and structural characteristics of the component, to which the other sample element is fixed, are taken into account in the test result. Furthermore, it is possible to work with a smaller sample element than the known testing methods allow.

In order to carry out the load test, a tensile element can be fixed by means of adhesive to the other sample element, which tensile element extends into a tubular support element, which is supported on the reference component while surrounding the other sample element. Such apparatuses for carrying out load tests are already known and are sold, for example, by DeFelsco Corporation, New York, U.S.A., under the names PosiTest AT-A Automatic and PosiTest AT-A Manual.

In this test set-up, for the joining of tensile element and sample element, an adhesive joint having greater adhesive force than the adhesive joint between sample element and component is provided, in order to ensure that, in the event of an overloading of one of the adhesive joints, the one between sample element and component breaks first. These different adhesive forces of the adhesive joints can be achieved, for example, by designing the surface of the sample element, which faces the reference component and which is coated with adhesive, to be smaller than the total area of the sample element.

When the method according to the invention is used in preparation for the repair of a damaged area on said one component, preferably material is removed in the area of the damage, and the edge of the removed area is made to taper, so that a recess with slanted external edges is created, into which the repair element is subsequently inserted and joined to the component. In order to carry out the testing method, the sample element is fixed in the removed section and then subjected to tensile loading.

Because the loading test is carried out in the damaged area, the test also takes into account the component's material properties and structural properties in the damaged area which exist at the surface and/or in the internal structure of the component, and which were particularly caused by the damaged area.

After carrying out the testing method according to the invention, the other sample element can be separated from the reference component by means of a wedge element, and the wedge test known per se can thus additionally be carried out.

BRIEF DESCRIPTION OF THE DRAWINGS

The invention is explained in greater detail below by reference to the FIGURE showing a schematic and greatly simplified exemplary embodiment.

DETAILED DESCRIPTION OF THE PREFERRED EMBODIMENTS

The only FIGURE is a schematic representation of a section of a component 1 made of FRP, for example a section of an aircraft fuselage. The upper face of this component part had a damaged area not shown, which is to be repaired. To this end, material was removed in the area 2 of the damage, and the edges 3 where the area 2 transitions into the upper face of the component 1 were made to taper by means of scarfing, in order to insert into the thus-created recess in a conventional manner a repair element not shown, and fix it in place by means of adhesive.

In order to test the fracture toughness of the adhesive joint to be formed between component 1 and repair element, as depicted in the FIGURE, a sample element 5, made of the same material as the repair element to be used, is fixed by means of an adhesive layer 6 to the bottom of the removed area 2, wherein the same adhesive is used as is also used for the subsequent fixing of the repair element. Affixed as a tensile element to the upper side of the sample element 5 by means of an adhesive layer 7 is the stamp 8 of a testing apparatus, for example from the known apparatus PosiTest AT-A Automatic by DeFelsco Corporation, New York, U.S.A. The tensile element, or rather the stamp 8, extends into a tubular support element, which is supported on the component 1 while surrounding the sample element 5.

In order to ensure that the adhesive force between stamp 8 and sample element 5 is greater than the adhesive force between sample element 5 and component 1, the effective adhesive layer 6 between sample element 5 and component 1 can be reduced compared to the size of the adhesive layer 7, for example by laying separating foils 10, for example, one or two circular, ring-shaped separating foils, in the edge area of the sample element 5, between adhesive layer 6 and component 1, which prevent contact between the adhesive layer 6 and the component 1.

After curing of the adhesive layers 6 and 7 (or, if appropriate, also of the layers of the sample element 5), a tensile force is applied via the stamp 8, as indicated by the arrow, and this tensile force is increased up to a pre-defined limit value, wherein the support element of the testing apparatus is supported on the component 1 or on the separating foil 10. If the adhesive joint between sample element 5 and component 1 holds up to this limit value, then it may be assumed that the corresponding adhesive layer, which joins the repair element to be inserted to the component 1, likewise has sufficient fracture toughness.

In order to remove the sample element 5, including the stamp 8, from the component 1 after the described test has been carried out, a wedge element 12 can be used, of the sort also used to carry out the known wedge test, to thus additionally test the adhesive power of the adhesive joint.

As the FIGURE schematically shows, such a testing method can also be carried out on the unchanged outer surface of the component 1, if appropriate, parallel to the fixation of the repair element. This is depicted by the sample element 5', which is mounted via an adhesive layer 6' (and, if appropriate, separating foils 10') on the unchanged upper face beyond the edges 3 of the area 2 of the component 1. Any existing layers of paint must be removed beforehand. The sample element 5', in turn, has fixed to it by means of an adhesive layer 7' a tensile element in the form of a stamp 8'.

This procedure allows the repair element to be inserted into the area 2 and the sample element 5' to be sourced from the same batch of produced components. In the same way, the adhesive layers 6', 7', with which the sample element 5' is fixed, and the adhesive layer for fixing the repair element can derive from the same batch of adhesive. As a result, the test joint and the actual adhesive joint are more comparable, and repairing and testing can be carried out in parallel.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A method for testing the fracture toughness of an adhesive joint to be formed between two components made of fiber-reinforced plastic comprising the steps:
   providing a first component and a second component of a joint to be formed, first and second components being made of fiber reinforced plastic,
   forming a test joint between first and second sample elements and
   applying a tensile load to this test joint until a pre-defined value is reached,
   wherein the first sample element is the first components and the second sample element is different from the second component, and
   wherein the step of applying a tensile load comprises applying the tensile load on the second sample element.

2. The method according to claim 1, wherein the second sample element is circular.

3. The method according to claim 2, wherein the second sample element has a diameter of 8 mm to 60 mm.

4. The method according to claim 2, wherein the second sample element has a diameter of 10 mm to 50 mm.

5. The method according to claim 1, wherein a tensile element is fixed by means of adhesive to the second sample element, and wherein the tensile element extends into a tubular support element, which is supported on the first component while surrounding the second sample element.

6. The method according to claim 5, wherein the adhesive force of the adhesive joint between the second sample element and the tensile element is greater than the adhesive force of the adhesive joint between the second sample element and said first component.

7. The method according to claim 6, wherein the surface of the second sample element which faces the first component, and which is coated with adhesive, is smaller than a total area of the second sample element.

8. The method according to claim 1, wherein, after carrying out the testing method, a further step is performed of separating the second sample element from said first component by means of a wedge element, and at the same time, performing a wedge test.

9. A method for preparing for the repair of a damaged area on a component made of fiber-reinforced plastic, comprising the steps:
   providing a component made of fiber reinforced plastic and comprising a damaged area that is to be repaired,
   removing material in the damaged area and tapering an edge of the damaged area where the material was removed,
   forming a test adhesive joint between a sample element and the component in the damaged area after removal of the material, and
   applying a tensile load on the sample element of the test adhesive joint until a pre-defined value is reached.

* * * * *